United States Patent
Britton et al.

(10) Patent No.: US 6,315,113 B1
(45) Date of Patent: Nov. 13, 2001

(54) CHEMICAL DISPOSAL OF MEDICAL SYRINGE NEEDLES AND OTHER HAZARDOUS SHARPS

(76) Inventors: Richard B. Britton, P.O. Box 7451, Charlottesville, VA (US) 22906-7451; Malcolm P. Woodward, P.O. Box 6701, Charlottesville, VA (US) 22906

( * ) Notice: Subject to any disclaimer, the term of this patent is extended or adjusted under 35 U.S.C. 154(b) by 0 days.

(21) Appl. No.: 09/106,455

(22) Filed: Jun. 30, 1998

Related U.S. Application Data
(60) Provisional application No. 60/051,189, filed on Jun. 30, 1997.

(51) Int. Cl.$^7$ .................................................. B65D 81/24
(52) U.S. Cl. .......................... 206/210; 206/366; 604/110; 204/275
(58) Field of Search ..................................... 206/366, 210, 206/365; 604/110, 192, 263; 241/33, 46.017; 422/255, 292, 301; 204/275

(56) References Cited

U.S. PATENT DOCUMENTS

| | | | |
|---|---|---|---|
| 4,752,364 | * | 6/1988 | Dhooge ................................ 204/151 |
| 4,925,540 | * | 5/1990 | Dhooge ............................ 204/157.42 |
| 5,038,929 | * | 9/1991 | Kubofcik ............................... 206/210 |
| 5,047,224 | * | 9/1991 | Dhooge ................................. 423/437 |
| 5,084,027 | * | 1/1992 | Bernard ................................. 604/192 |
| 5,437,656 | * | 8/1995 | Shikani et al. ....................... 604/89.1 |
| 5,441,622 | * | 8/1995 | Langford .............................. 204/275 |
| 5,639,031 | * | 6/1997 | Wright et al. .......................... 241/33 |
| 5,687,839 | * | 11/1997 | Gnau, III et al. ..................... 206/204 |
| 5,758,775 | * | 6/1998 | Lowe ................................... 206/571 |

FOREIGN PATENT DOCUMENTS

2687320 * 8/1993 (FR) ..................................... 604/110

* cited by examiner

*Primary Examiner*—John G. Weiss
*Assistant Examiner*—V. Srivastava

(57) ABSTRACT

This disclosure describes a chemical process for dissolving medical sharps such as syringe needles, suture needles, lancets and the like. Several reagents are described with various strengths suitable for use in a syringe cap or for use in a bulk disposal container. Several types of disposing caps for syringe needles are disclosed, and also several types of containers for the disposal of bulk syringes and medical sharps.

18 Claims, 15 Drawing Sheets

CHEMICAL DISPOSAL OF MEDICAL SYRINGE NEEDLES AND OTHER HAZARDOUS SHARPS

REFERENCE TO PRIOR DISCLOSURES

This application is filed with reference to a prior Document Disclosure #386744, entitled Chemical Disposal of Medical Sharps Including Syringes, Lancets, Scalpels, and the Like filed Dec. 28, 1995.

This application is also filed with reference to a Provisional patent application # 60/051,189 entitled Chemical Disposal Process for Medical Sharps: Syringe Needles, Lancets, Scalpels, and the Like. and filed Jun. 30, 1997.

FIELD OF THE INVENTION

This invention relates to chemical processes for disposing of medical and surgical sharps, such as hypodermic syringe needles, lancets, scalpels and the like. It relates further to means for applying the process to syringe needles after use. It relates still further to disposal boxes for applying the chemical disposal process to used and contaminated medical sharps.

BACKGROUND OF THE INVENTION

During the routine use of medical hypodermic syringes millions of times per day in the United States an abnormally high number of accidental needle sticks and injuries from needles occur. These small wounds to medical personnel and others are often contaminated with blood residue which can possibly carry an infectious or deadly disease. This threat has so alarmed the medical world and the public that hundreds of inventions have been devised in the last few years that address this issue, and there are now numerous patents issued that describe mechanical means and safety mechanisms to ameliorate this problem and reduce the risk of inadvertent contact with contaminated medical sharps.

Without question the risks and potential for injuries from an expended and contaminated medical sharp is both immediate in its first use, and is also long range in its final disposition as hazardous medical waste. This situation requires elaborate procedures in handling, sterilizing and final disposal such as with incineration which is in itself a problem and not a solution. Incineration can destroy the biological hazard but at high social cost. Incineration is expensive and requires large capital costs, requires a specialized facility which is expensive to build, specialized equipment which is additionally expensive, energy wasteful and increases air pollution.

Incineration operates at very high temperatures of many thousands of degrees Fahrenheit which is required for the incineration of stainless steel and which in turn often fuses materials creating new toxic compounds in the process. Other disposition practices such as microwaving, steam sterilizing, chemical and biologic treatment, or in the end, landfilling, are also complicated and expensive. Landfilling medical wastes buries the problem but is not a perfect disposal due to the destruction of real estate, abusive over use by communities, leachate flows, and the possibility of re-exposure of the hazard by gassing outflows, deluges of water, or land cover removal. Throughout the transport and the current disposal process the medical sharp remains potentially infectious and hazardous to everyone concerned. There is a high degree of risk for everyone exposed, and at a high cost for such items as medical waste for its special handling and disposal.

In the prior art we note that the emphasis is on safety caps and covers over syringe needles by mechanical means. There are many excellent examples filed in Class 604 which show mechanical covers and other means of disposing of needles after they have been used and several practical and superior methods are cited. Very few references are found wherein a solution is introduced to the needle after use.

The best example is in a two stage interacting process contained in the cap, in the U.S. Pat. No. 5,322,165 issued to Melker et al Jun. 21, 1994 wherein one stage contains a disinfectant solution. In the U.S. Pat. No. 5,188,614 issued to Charles Hart Feb. 23, 1993 there is disclosed the use of a manually replaced cap containing two chambers that when pierced activate a foaming plastic.

Similar prior art is seen in U.S. Pat. No. 5,084,027 issued to Bernard Jan. 28, 1992 which has a cap containing three compartments with resins in two, and cotton wool in the third that activate and enclose the needle in a protective hardening material. There is no evidence herein of more than a disinfectant being applied.

In the prior art showing best means to cover the needle and its sharp point, we see a good example in Wesson et al, U.S. Pat. No. 4,994,046 issued Feb. 19, 1991, which discloses a slide over cover that secures in place over the needle after use. In the prior art there are also hinged caps that rotate over the needle after use which protect and shield the sharp point such as U.S. Pat. No. 4,982,842 issued to Hollister, Jan. 9, 1991. Hollister references 85 patents in his patents. In U.S. Pat. No. 5,197,954 issued to Cameron, Mar. 30, 1993, a needle is sheared off and swings back alongside the syringe case after use, and optionally may be disinfected. Another invention disclosing a means to disinfect is introduced as a solution to the risk of needle contamination in U.S. Pat. No. 5,383,862 issued to Berndt et al Jan. 24, 1995. It discloses the use of a separate protecting disinfecting pouch that covers and contains the needle. Applications of disinfectant are useful but no disinfectant procedure above can satisfactorily eliminate the potential threat and problem of infectious blood material being encapsulated within the needle and held dormant in place by the capillary action of the disinfectant Another prior art in Class 604/259 that we address is in the separate container systems located on desktops, counter tops, patient's rooms, nurse's stations, doctor's and dentist's offices, and even in homes when needles are in use, wherein the medical sharp is transported over to these containers to be disposed of. Such container systems including storage boxes to be used for a later disposal are now routine items in hospitals, clinics, and homes, and even in the emergency rooms as well as the mobile care and rescue units. The example that we cite is in U.S. Pat. No. 5,038,938 issued to Berndt Aug. 13, 1991, which discloses a disposable tray assembly housing a sealed reservoir of disinfectant that is accessed through an elastomeric plug. Any container with only a disinfectant will leave the medical sharps intact which can still stick you through the walls of a container when being handled in a normal manner for commercial or household waste.

SUMMARY OF THE INVENTION

Medical sharps such as syringe needles, lancets, suture needles, scalpels and the like are generally manufactured from stainless steel. "Stainless steel" is a term applied to a broad group of alloys of iron which contain 10 percent or more of chromium, an amount sufficient to greatly retard normal rusting and corrosion now more common from impure rain water condensation and other induced contaminants. Stainless steel is neither a specific nor an absolute term and merely indicates such a metal is less corrodable than common metals such as iron or carbon steel. Chemicals that will dissolve a solid material (usually a metal) are referred to as etchants by the metals industries. In this specification such chemicals will be referred to hereinafter as dissolvents, since their purpose here is to completely dissolve a metal sharp, as compared with the metal industry's purpose of determining grain structure.

Stainless steels are resistant to acids, salts, and alkalis and are therefore quite durable even when exposed to the dirty environment of a city dump. Thus it seemed desirable to develop a dissolvent that could eat away a medical sharp and remove the mechanical hazard of the sharp metal from our environment for all time.

Since we had to consider the types of medical stainless steels in this invention, we experimented with a variety of chemicals to see if we could find a method satisfactory and safe for corroding away the medical sharps to make them harmless. Several suitable chemical dissolvents were ultimately found that can dull a sharp immediately and dissolve a typical syringe needle in a few minutes.

This invention is thus a process for chemically disposing of a thin medical sharp with a chemical dissolvent, the dissolvent being sufficiently benign that it does not contaminate the environment. Many types of medical sharps were considered in this invention and a series of chemical solutions were developed with various effectiveness and strength. Dissolvents were formulated that can dull and remove the "sharp" surfaces instantly, dissolving into a solution in a few minutes, completely eliminating the needle in less than 30 minutes for disposal. A safe and acceptable level of chemicals in solution was achieved with these results, and although faster results are possible, the solutions and concentrations become too caustic and uncomfortable to use safely. We have achieved usable solutions that are "mild" and safe in our dissolvent process, yet extremely active with the inclusion of the stainless steel material.

A group of mechanisms were also invented for applying the dissolvent to a sharp wherein they are covered and shielded in a box or container until the chemical process has run to completion. A containment box may be of a size sufficient to hold scores or more of spent medical syringes and many hundreds of lancets wherein they are dissolved, and safely transportable into the normal waste disposal. In certain disposal situations an anti-dissolvent may be introduced to neutralize the chemical activity prior to its final disposal.

A color indicator can be included in the solutions for the situation wherein a clear line or section is marked off and provided in the side of the containment box so that the indicator shows when the dissolvent is active and when it is consumed and inactive.

Various absorbent materials were provided in situations to contain the dissolvent and control leakage or spillage in such containment boxes with satisfactory results. Such absorbent was found to have very little effect upon the speed of reation. This type of disposal process using a containment box and dissolvent solution offers an excellent means to safely dispose of medical sharps.

DETAILED DESCRIPTION OF THE INVENTION

Figure 1:
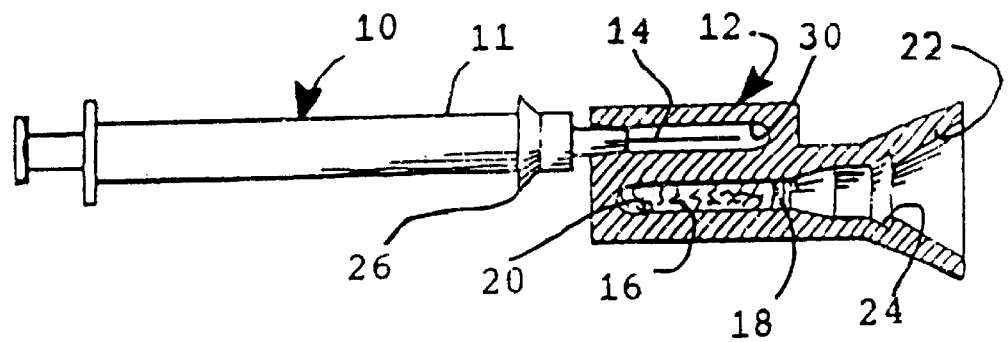
FIG. 1. This is a partially sectioned view of a hypodermic syringe with its reversible disposing dual cap in place.

There are several types of medical sharps that are of a concern here, namely hollow needles that are widely used for injection with syringes, solid needles that are used for suturing, tiny knives such as lancets that are used for obtaining blood samples, and scalpels that are used for all types of surgical cutting. These puncturing and cutting instruments that are used in medical procedures are generally inexpensive and thrown away after use. This has created a disposal problem which our invention can solve.

Syringe needles are made from a ductile metal that can be drawn to extreme thinness, is capable of being sharpened to the good edge, and has sufficient tensile strength to resist being bent. Suture needles can be less ductile, but they must retain a sharp point during repetitive use. Cutting tools must retain an extremely sharp edge, but they can usually be made thicker to reduce their requirement for tensile strength.

In all these applications the material should resist corrosion during long term storage prior to use, and also during use, and such material should have no brittleness whereby a sharp might snap off and embed in a patient or medical worker. Due to the need for corrosion resistance, these examples and other medical instruments and tools are now generally manufactured from a stainless type of steel.

Stainless steel is a generic term used to describe a group of 130 commercial types of iron-base alloy steels typed by the American Iron and Steel Institute (AISI) and listed in Materials Selector 1987, a Materials Engineering Journal by Penton Publishing, Inc. Stainless steels exhibit high resistance to corrosion and rusting due to an alloy content of chromium between 10 and 27%. Additional corrosion resistance is often obtained in these alloys by the inclusion of nickel up to 19% and other elements and by holding the carbon content low, generally below 0.1%.

Stainless steels may be classified into at least three groups; austenitic, ferritic, and martensitic. Ferritic and martensitic steels are usually ferromagnetic while austenitic is not. Ferritic cannot be hardened while martensitic can be hardened by heat treatment One stainless that was in use in 1987 for surgical instruments and knives is AISI Type 420, a magnetic, martensitic stainless steel comprising:

| | |
|---|---|
| Carbon | >0.15% |
| Chromium | 12.0–14.0% |
| Manganese | 1.00% max. |
| Phosphorus | 0.040% max. |
| Sulfur | 0.030% max. |
| Silicon | 1.00% max. |
| Iron | Balance, approx. 85 to 87% |

Other stainless steels with minor differences in composition from 420 include Types 410 and 414, both of which are used for tubing. Type 414 is used also for knife blades and for products requiring springiness or high tensile strength. Type 440A is used for cutlery and instruments. Stainless steel such as 410, 414, and 420 exhibit good resistance to weather and water, and to most chemicals and chemical solutions. From the uses described in the Materials Selector, it was deduced that the stainless used for needles and the smaller medical sharps is most probably one of the above mentioned AISI type 400 series alloys.

A dissolvent is "a solvent capable of dissolving another substance" according to The Random House Unabridged Dictionary. In our experiments to find a suitable dissolvent, we searched for a chemical that is low in toxicity to humans and yet capable of rapidity dissolving away a medical sharp. The amount of dissolvent needed to dissolve a sharp was found to be no more than three to five times the volume of the sharp itself, and precautions were taken to contain and encapsulate the dissolvent around the sharp. We wanted a benign process that would not threaten or endanger the human system if leakage occurred. We have achieved these ends with the invention of a dissolvent that is safe.

Initial tests were run on syringes known as type U-100 made by Becton Dickinson and Company typically for daily or twice daily home use insulin injections. The needles are ferromagnetic, V-28 gauge which has an outside diameter of 0.0142 inches, and a working length of 0.5 inches. These are described as having MICRO-BONDED™ lubricant which would appear to indicate they are coated to reduce friction during insertion. These syringes are sold as disposable and intended to be used once and discarded. Since their retail cost is low, less than 20 cents each in a box of 100, this expense is small compared with other medical costs. Our dissolvent is equally inexpensive and would add no cost burden to any application.

Tests were also run on U-100 Insulin Syringes having 29 gauge needles and described as Monoject. These syringes are manufactured by Sherwood Medical, St. Louis, Mo. 63103.

Initial tests were run on said syringes using dilute sulfuric acid $H_2SO_4$ of specific gravity 1.25 (battery acid), and the test results were erratic. In some tests the needle would etch away, break off and fall away from the syringe in 4 hours while in other tests, equivalent etching would take up to 48 hours. It is believed that a coating on the needles resisted the solution, causing the longer times while in other tests with faster results, flaws in the coating allowed the dissolvent to immediately reach the underlying metal.

Hydrochloric acid HCl in dilute solutions was tried next, and then solutions of HCl and ferric chloride—$FeCl_3$. HCl is present in the human stomach while $FeCl_3$ is a relatively innocuous chemical salt, and in combination they present a reasonably safe and low toxicity chemical solution.

In these tests the relative strengths of HCl to $FeCl_3$ was varied, and it was found that a solution of 3 parts $FeCl_3$ using a 25% solution in water, to 1 part HCl of a 12 molar solution, provides an dissolvent that will dissolve a needle in about 3 hours. Varying the proportions in either direction from 3:1 decreased the dissolvent speed.

Another dissolvent was found in a solution of acetic acid ($CH_3COOH$) with $FeCl_3$. Acetic acid is an organic chemical that is found in foods such as apple cider and added to foods such as pickles. A 5:1 solution of $FeCl_3$ with acetic acid dissolved test needles in about 12 hours.

With such suitable dissolvents it was determined that an absorbent would aid in containing the dissolvent around the sharp and greatly reduce or even eliminate altogether the chance of it spilling out of its capsule.

Two absorbents have been found that are satisfactory: wood cellulose (similar to sawdust) and cotton. Wood cellulose is commonly found in kitty litter as sold in pet shops for cat owners.

The dissolvent is soaked into the cellulose and may be sealed in by means of a plastic film or wax such as paraffin, or similar friable surface layer that can prevent leakage or evaporation prior to use.

After the syringe has been used, the cap is installed over the used needle whereby the needle is punched through the protective layer and is forced into the cellulose packing. The cap is preferably designed to be captured by the body of the syringe. It has also been found that the cellulose grips the needle extremely tightly once it is inserted, probably due to the immediate surface corrosion on the needle creating a high coefficient of friction with the cellulose.

A second absorbent is cotton which is packed into a cap and wetted with dissolvent which has the surface sealed over as in the wood cellulose example. Cotton displays two advantages over wood cellulose in that the dissolving reaction proceeds faster and that a color change is obtained that indicates when the reaction has been completed. The cotton begins as a white color, and turns yellow when the reaction begins and progresses to brown when the reaction is complete.

To aid in beginning the dissolution process, an abrasive may be combined with the absorbent to scratch and abrade the sharp as it is inserted into the absorbent. The abrasive should have a hardness that is greater than the hardness of the sharp. Suitable abrasives include any of those that are used to manufacture emery cloth and sandpaper such as alumina, any of the carbides, and harder varieties of sand.

With reference to the accompanying chart of tests, in a test using 1 cc, 29 gauge, ½ inch length, Insulin Syringes made by Sherwood Medical in St. Louis, Mo., totally dissolution of the needle was accomplished in 4.5 minutes. Stainless steel needles were individually placed in 10 cc test tubes at room temperature for this series of tests charted below. In all tests the needle was badly corroded in 4 minutes; and in Test #6, the needle broke off after 1 minute, 55 seconds and was totally dissolved in 4.5 minutes.

To apply the dissolvent to the medical sharp, we have invented several adaptive mechanical systems that apply to syringe needles, and note that in the prior art, many of the apparatae for capturing needles are useful with this process when in combination with them, our dissolvent and absorbent is used.

We offer several embodiments as shown herein that adapt to existing syringes and can adapt to related products as well as to other containers and disposal devices in the current use. Considering the very large number of disposable syringes sold each year that are inexpensive and simple to handle, a sensible adaptation can be achieved by incorporating the chemical disposal process to the existing manually applied cover cap in a "chemical process cap". This method should prove satisfactory for the many uses at home that are not at any undue risk as a hazard and with the chemical process cap, the needle is rendered harmless and may be then disposed of in the normal trash stream without the hazard to sanitation workers that present needles present.

Other more complex embodiments would be needed for a safety syringe in the situations of active and high risks and the more automatic and secure caps would be considered as a sensible safety measure when this chemical disposal process is installed in each. A simple addition of this invention's chemical disposal process to existing storage disposal containers can eliminate risks from these sources as well. With the addition of this invention's process the entire range of medical items in stainless steel that deal with blood products can be rendered safe and eliminated as a metal object. The formulation used in these procedures shall remain safe to use and to handle throughout the process which can eliminate the risk and the elaborate and expensive procedures currently in hand for medical sharps and other stainless steel that may be contaminated.

| | Needle Dissolution Tests | | | | |
|---|---|---|---|---|---|
| | HCL (50%) | HNO$_3$ (50%) | FeCL$_3$ | CrO$_3$ | Time |
| Test #1 | 1.5 cc | | .5 g | 12.9 g | 19 min. |
| Test #2 | 1 cc | | | 12.9 g | 22 min. |
| Test #3 | 3 cc | 3 cc | | | 6 min. |
| Test #4 | 3 cc | 3 cc | | | 9 ½ min. |
| Test #5 | 2 cc | 4 cc | .5 g | | 5 min. |
| Test #6 | 2 cc | 4 cc | | | 4 ½ min. |

DESCRIPTION OF THE PREFERRED EMBODIMENTS

The disposal method employed in this invention is that of chemical dissolution of a sharp al object until said object is completely chemically reduced into chemical solution.

1) In household, personal, and low activity uses, including patient's rooms and public access areas, a preferred dissolvent would contain acetic acid (commonly known as vinegar), ferric chloride, and water.
2) In private medical clinics, nurse's stations and more active use areas, including vehicles and mobile units, a preferred dissolvent would contain hydrochloric acid, ferric chloride, and water.
3) In high use areas, bulk disposal areas, and supervised areas such as operating and emergency rooms, a preferred and fast acting dissolvent would be the combination of 1 part hydrochloric, 2 parts nitric acid, ferric chloride, and water.

All dissolvent activities are safer with an absorbent material being used, and color indicators an be included where requisite.

Dissolvents containing nitric acid should not be used, however, with an absorbent containing cotton or cellulose due to the possibility of generating a nitrate compound which may be highly explosive. Alternative absorbents for nitric acid containing dissolvents are synthetic fibers known to resist nitric acid and various inorganic materials.

To replenish efficacy and proper strength, fresh dissolvent may be added as needed and when use is completed, a neutralizer can be added to remove its activity. The activity of each embodiment above can vary by strength of dissolvent as requisite.

For further inclusion from reference sources and in standard practice, a dissolvent of medical stainless steel can be effected by a 25% solution of sulfuric acid in a ferric chloride solution, using water as its medium to perform satisfactory work.

For other steel sharps made from high speed steel or steel containing high percentages of nickel, a mixture of nitric and hydrochloric acids in a water solution is used. A 45% solution of sulfuric acid is effective on nickel alloys.

Stainless steels used in hypodermic syringe needles and in lancets can be dissolved by several acids combined with chlorides and by combinations thereof. A solution of sulfuric acid in water with specific gravity 1.25 will dissolve away needles, but is erratic perhaps due to the coatings on the needles. Hydrochloric acid in solution with water at various strengths, combined with ferric chloride, was found to give much more consistent results. Acetic acid plus ferric chloride was also a workable dissolvent.

Figure 2:
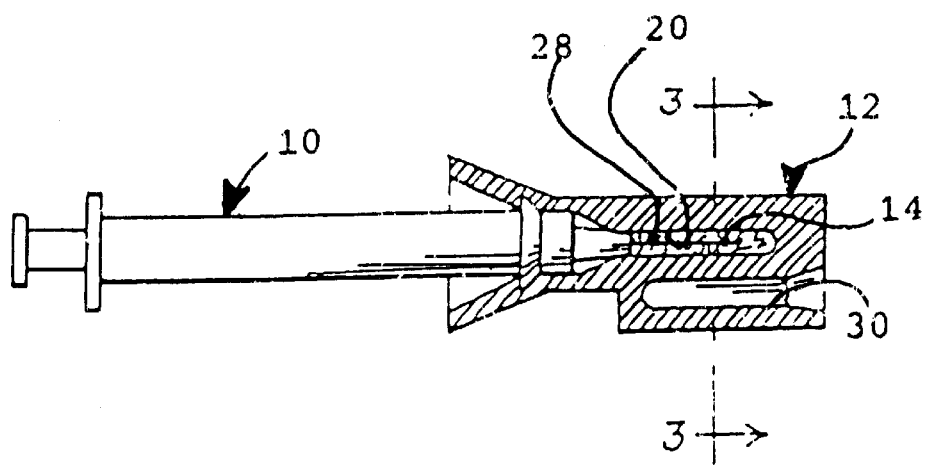
FIG. 2. This view shows the syringe of FIG. 1 with the reversible cap flipped and reinstalled to dispose of the needle.

Turning now to FIG. 1, there is shown a typical medical syringe 10 intended for one-time use. In sectional view there is shown attached to syringe 10 a reversible disposing cap 12 similar to the safety cap presently furnished with new syringes. Reversible disposing cap 12 serves to enclose and protect needle 14 as a normal safety cap prior to use of syringe 10. When cap 12 is removed for use of the syringe, and then reversed and reattached as shown in FIG. 2, it applies a dissolvent solution 16 retained in chamber 20 to needle 14. The dissolvent 16 is retained in chamber 20 of cap 12 by a layer of solid puncturable material 18. This puncturable material can be a wax such as paraffin wax, beeswax, or other material resistant to the dissolvent chemical action yet soft enough to be puncturable by the syringe needle when the cap is placed over it. A thin layer of a friable materials is also potentially suitable, or a plastic foil sealed in place. A flaring section 22 is attached to cap 12 to guide the disposing cap onto needle 14. Within flaring section 22 is a locking groove 24 which snaps elastically over locking ridge 26 attached to the barrel 28 of syringe 10 as cap 12 is fitted into place. Within chamber 20, an absorbent 28 such as cotton or sawdust or other material resistant to chemical action from the dissolvent may be fitted.

The minimize the use of possibly hazardous material, the volume of chamber 20 is on the order of three to six times the volume of needle 14, such quantity of absorbent being sufficient to completely dissolve needle 14.

Figure 3:
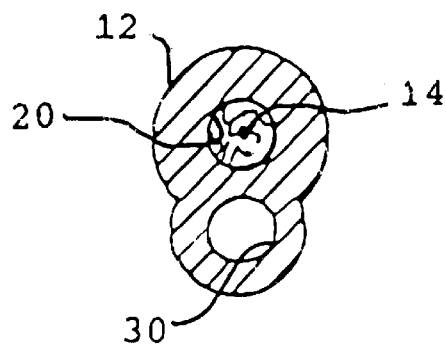
FIG. 3. A cross section view of FIGS. 2 and 5 along sectional line 3—3.

A cross section taken through cap 12 along line 3—3 of FIG. 2 is illustrated in FIG. 3, showing the position of needle 14 within safety chamber 30 prior to typical use of syringe 10. Also shown is needle 14' in chamber 20 containing absorbent 28 saturated with dissolvent 16.

Figure 4:
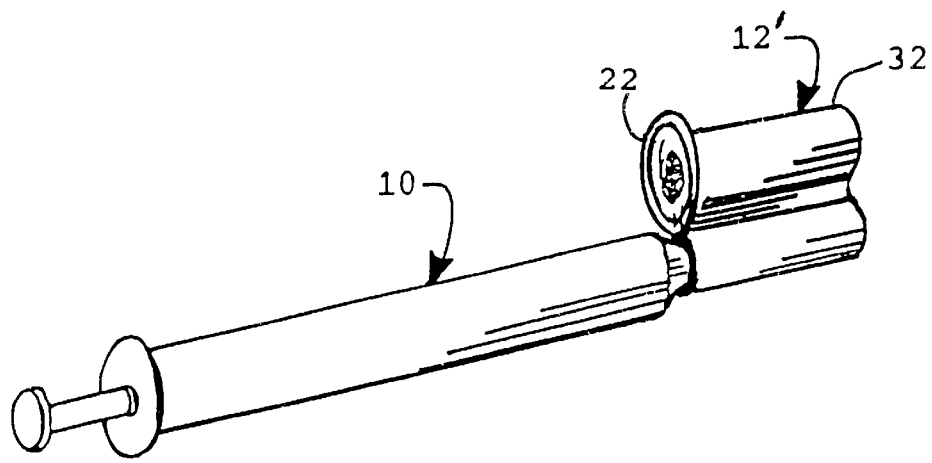
FIG. 4. A perspective view of another embodiment (preferred) of a disposing dual cap installed on a medical syringe.
Figure 5:
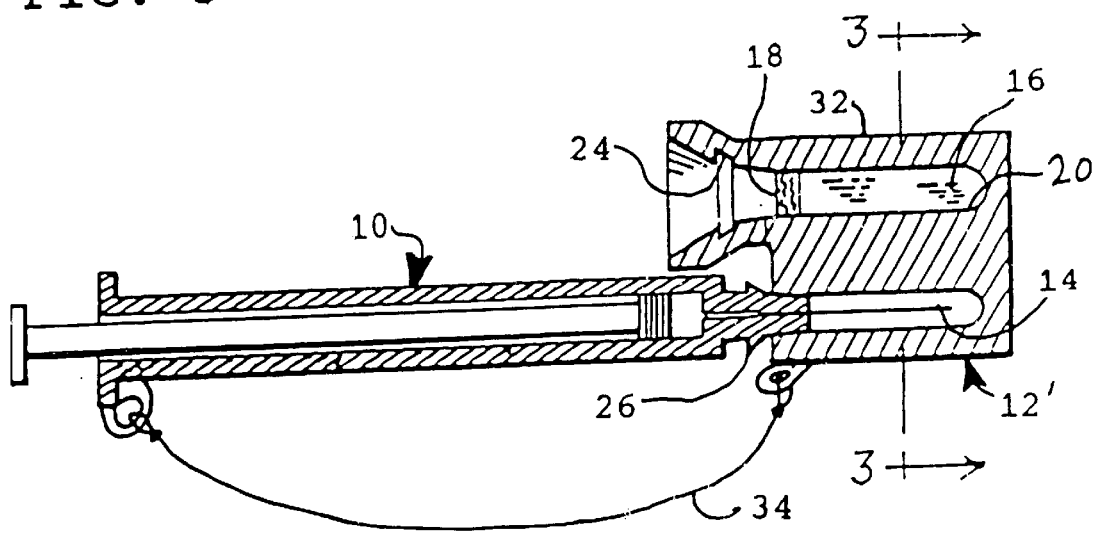
FIG. 5. A cross sectional view of the syringe and disposing dual cap of FIG. 4.

In FIGS. 4 and 5 is shown a syringe 10 with a preferred embodiment of a disposing cap 12'. In this embodiment, disposing section 32 is reversed from the embodiment of FIGS. 1 and 2 for greater ease of re-fitment of cap 12'. Lanyard 34 is provided to retain cap 12' while using the syringe.

Figure 6:
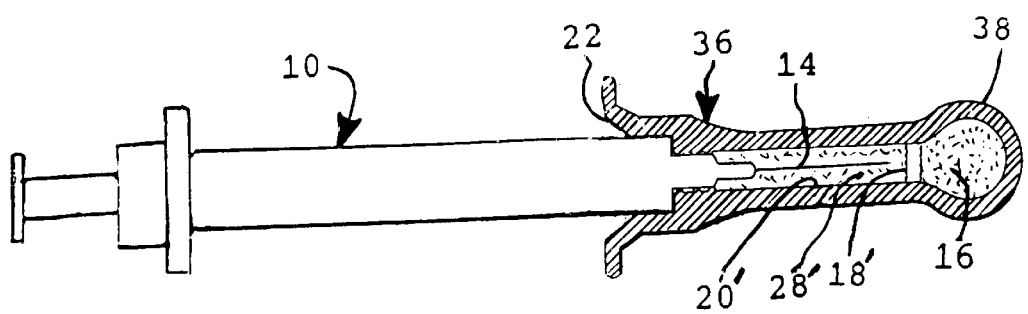
FIG. 6. A partially sectioned view of another embodiment of a medical syringe with a disposing squeeze cap, illustrated before disposal.

FIG. 6 illustrates again a syringe 10 as shown previously but here fitted with a dual purpose disposing cap 36 which is designed to protect the needle 14 prior to use and then be refitted in the same way to needle 14 after use of the syringe. Flare 22 aids in this refitting. A squeeze bulb 38 on the end of cap 14 contains dissolvent 16 which is ejectable through friable membrane 18' into chamber 20'. Chamber 20' may contain an absorbent 28 which is initially sterile before ejection of the dissolvent from bulb 38 into chamber 20'.

Figure 7:
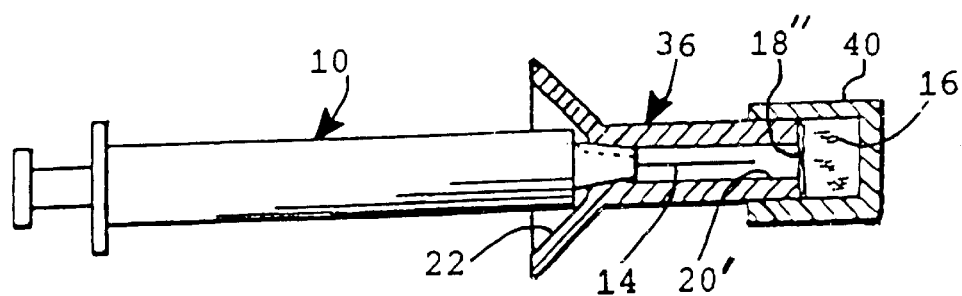
FIG. 7. A partially sectioned view of yet another embodiment of a medical syringe with a piston disposing cap.

FIG. 7 illustrates another embodiment of a disposing cap 36' for a syringe 10. Cap 36' provides initial safety use on syringe needle 14, and is refittable after syringe use by means of flare 22 and locking means not shown. A piston cap 40 containing dissolvent 16 is provided over the end of cap 36', which piston cap 40 can be forced further onto cap 36' to eject dissolvent 16 through friable membrane 18' into chamber 20'.

Figure 8:
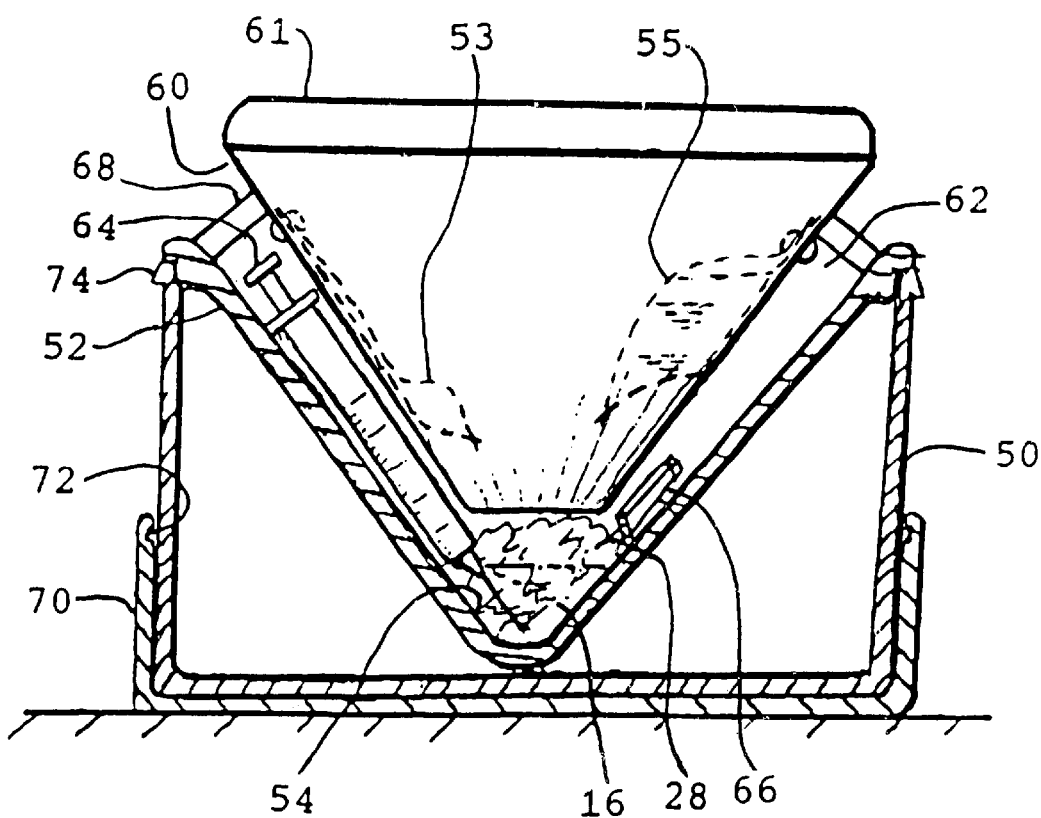
FIG. 8. This is a partial sectional view of a syringe disposal container designed to hold waste syringes in bulk FIG. 9. This is a perspective view of a conical container with single entry for syringes topping with lid wherein the needle is placed point down through the top opening.
Figure 9:
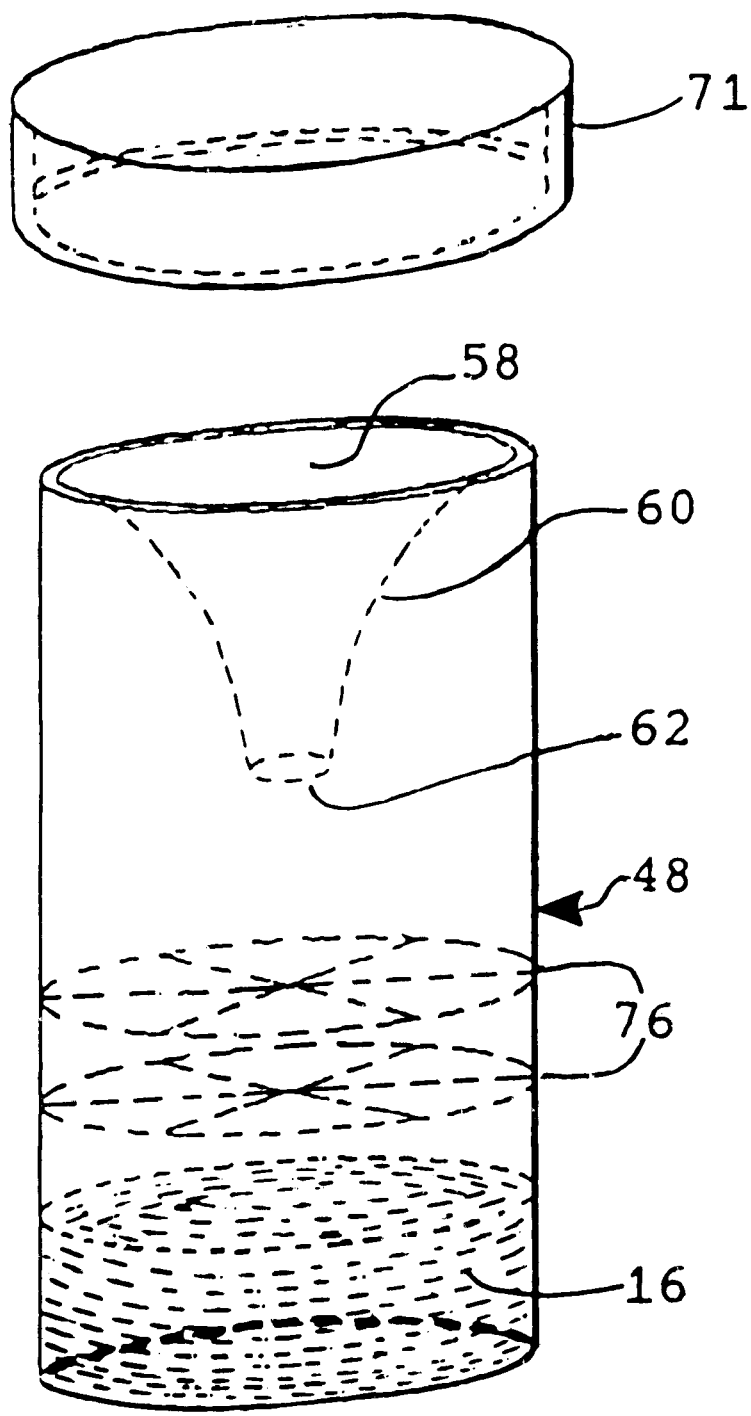
Figure 10:
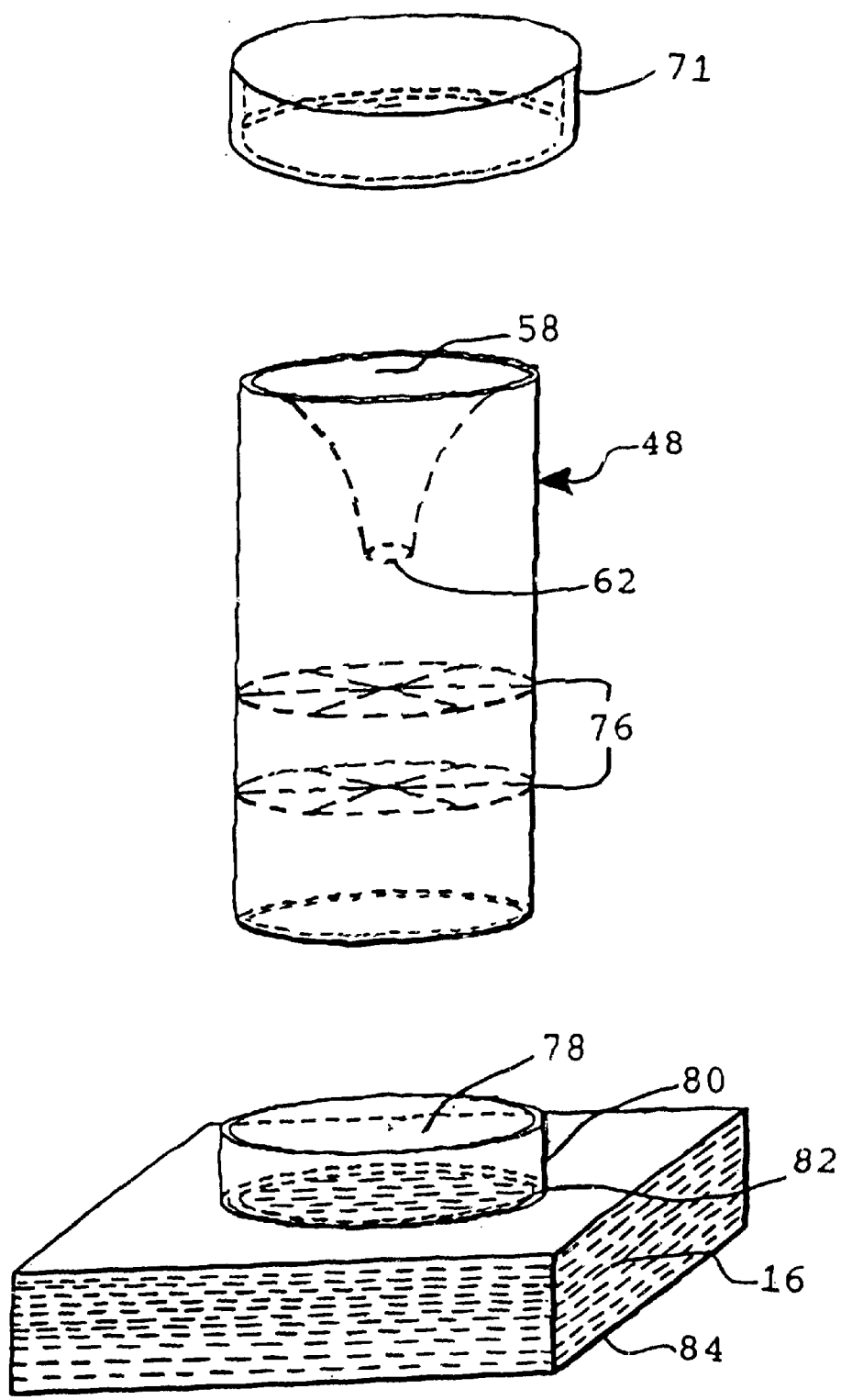
FIG. 10. This is a perspective view showing a typical single syringe disposal container in two sections.
Figure 11:
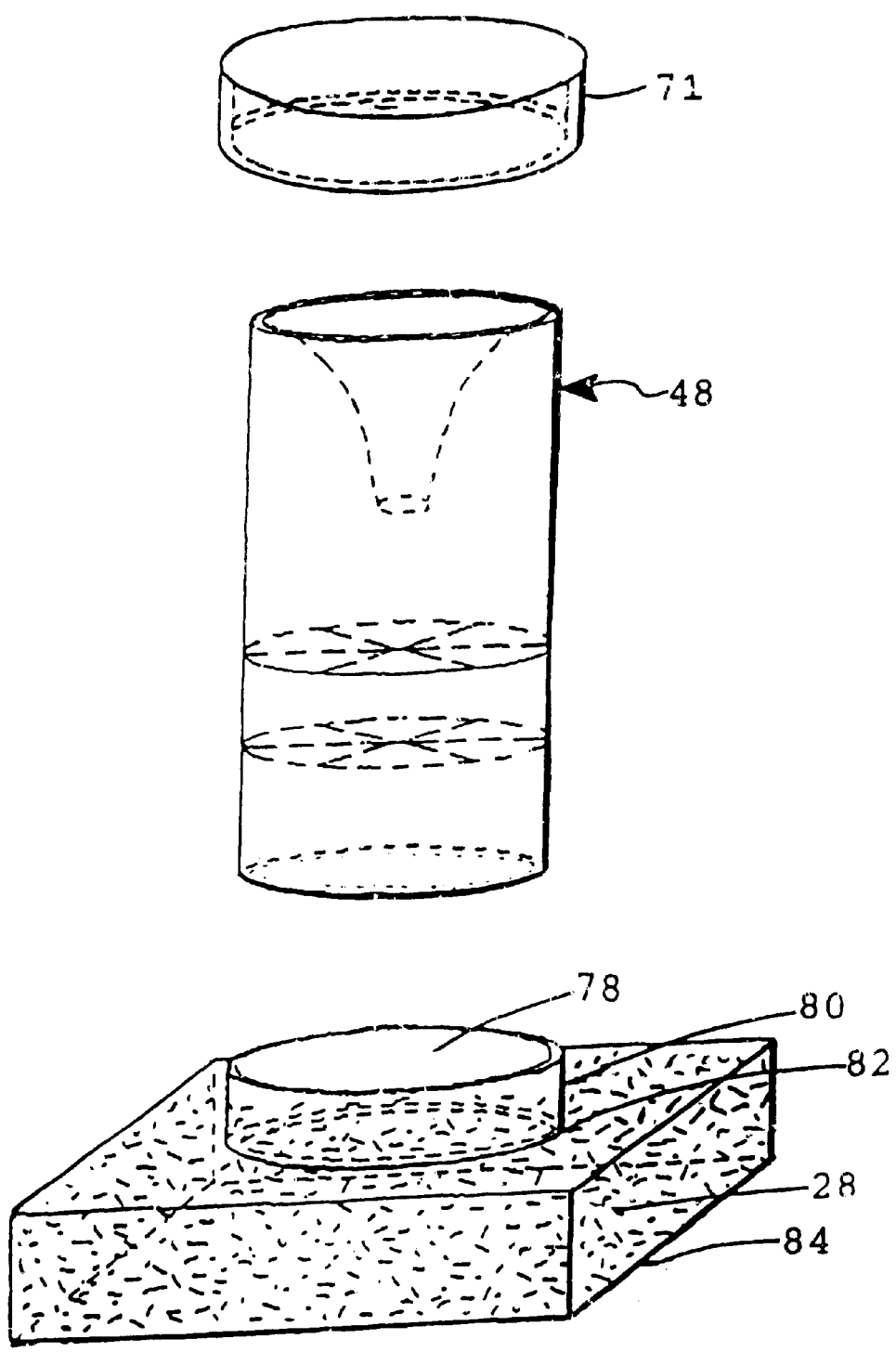
FIG. 11. This is a perspective view as in FIG. 10 which shows the base section filled with a dissolvent solution.
Figure 12:
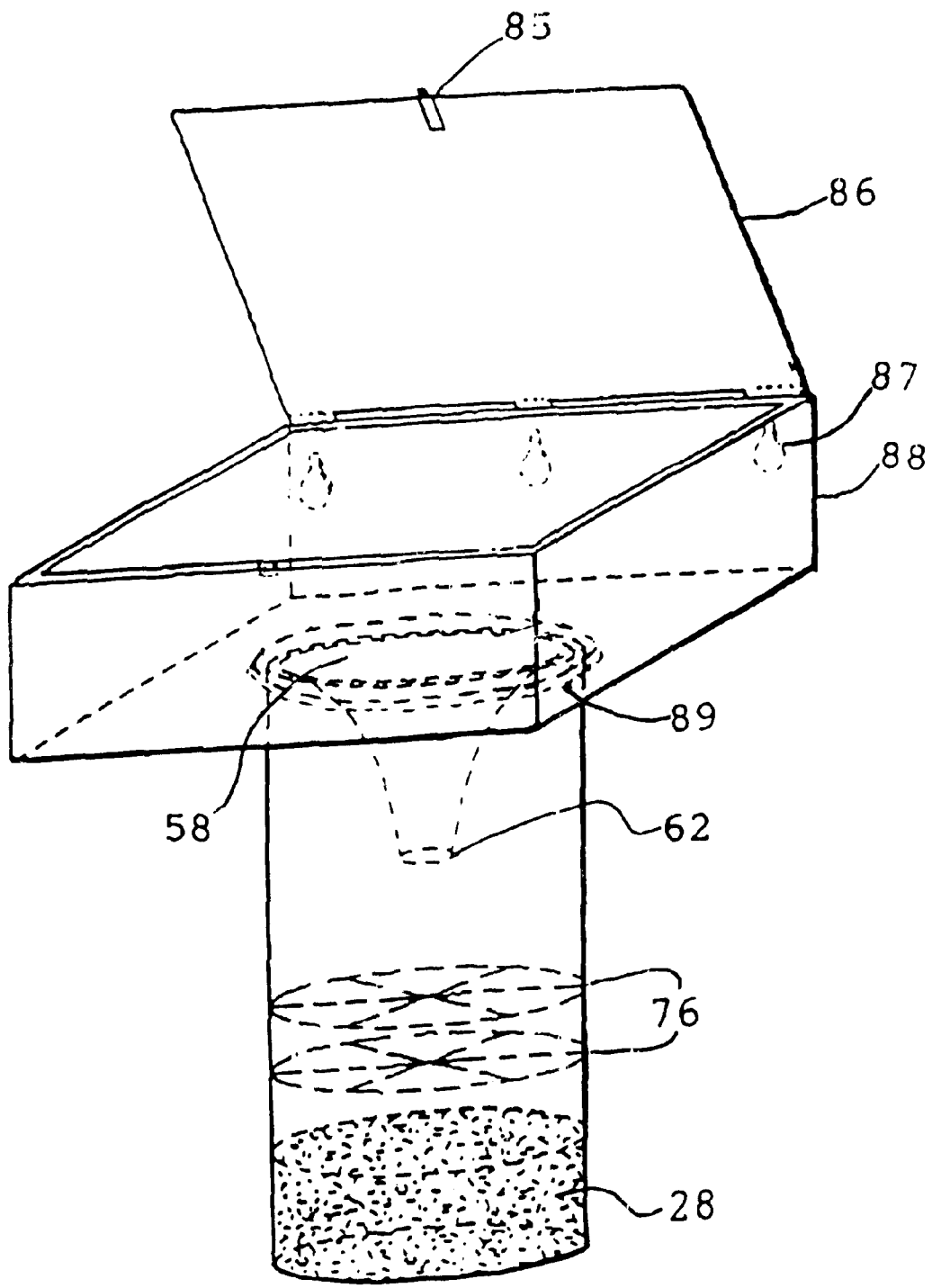
FIG. 12. This is a perspective view of a typical wall mounted syringe disposal container in two sections.
Figure 13:
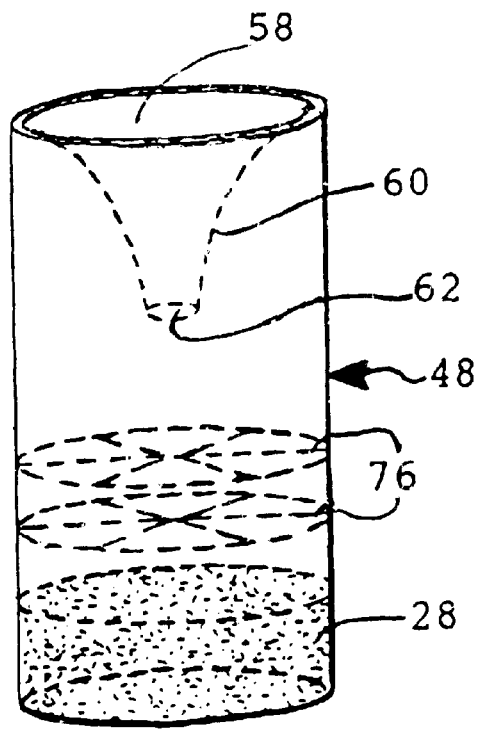
FIG. 13. This is a perspective view of a single entry syringe disposal container with dissolvent and absorbent.
Figure 14:
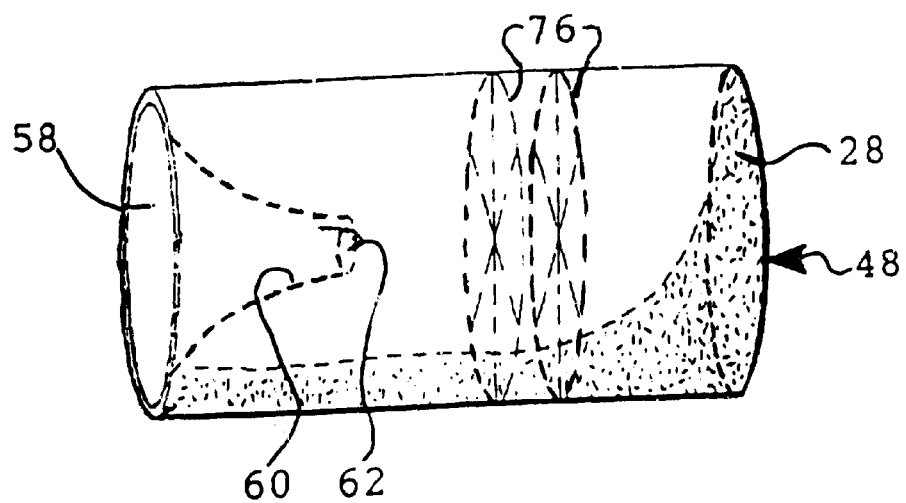
FIG. 14. This is a side perspective view of a typical disposal container being tipped-over on its side and showing the dissolvent and absorbent draining toward the entry opening.
Figure 15:
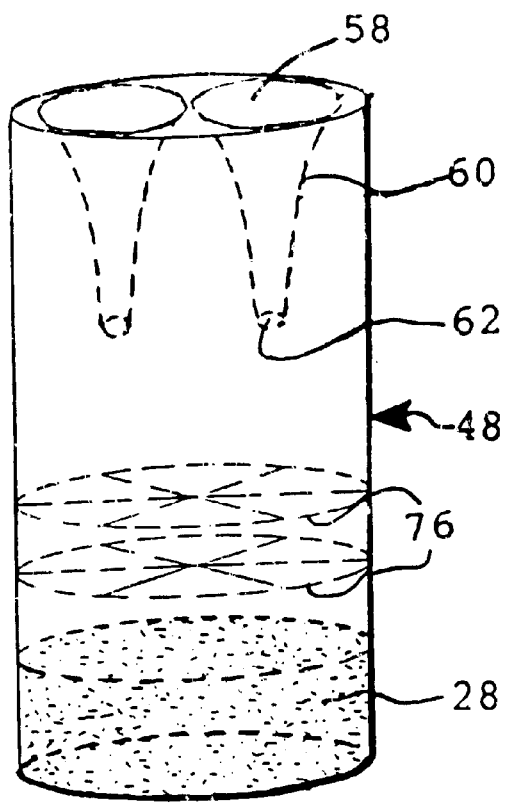
FIG. 15. This is a perspective view as in FIG. 14 with dual conical entries typical of a plurality of entries.
Figure 16:
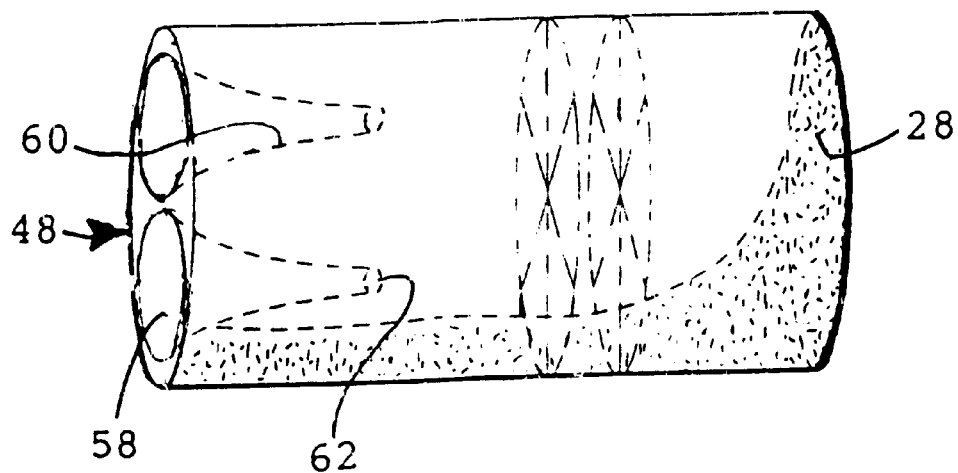
FIG. 16. This is a side perspective view as in FIG. 14 with the dual entries as in FIG. 18 above showing the container being tipped over.
Figure 17:
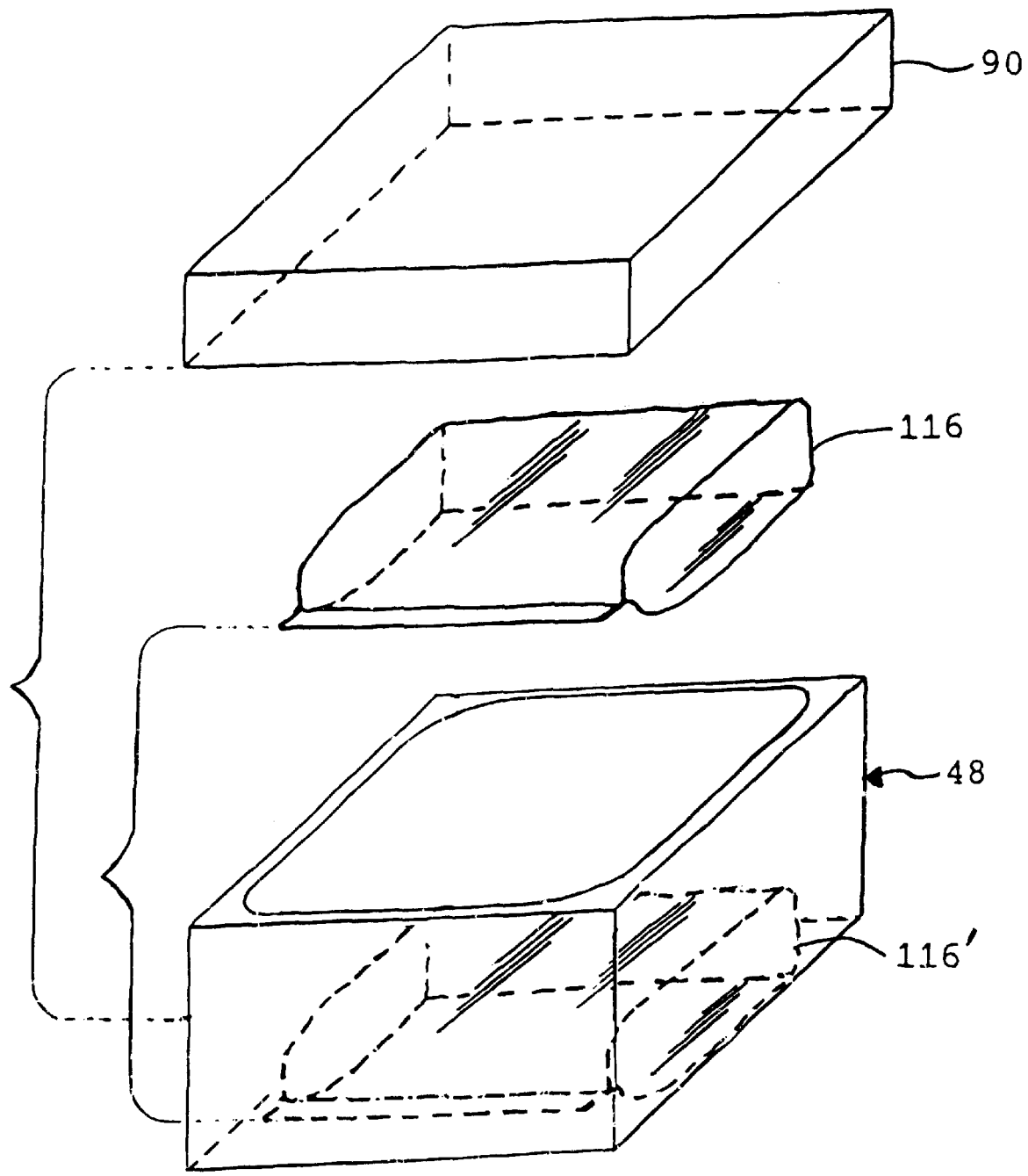
FIG. 17. This is a perspective view of a lid for the box or a tray as in FIG. 15 below.
Figure 18:
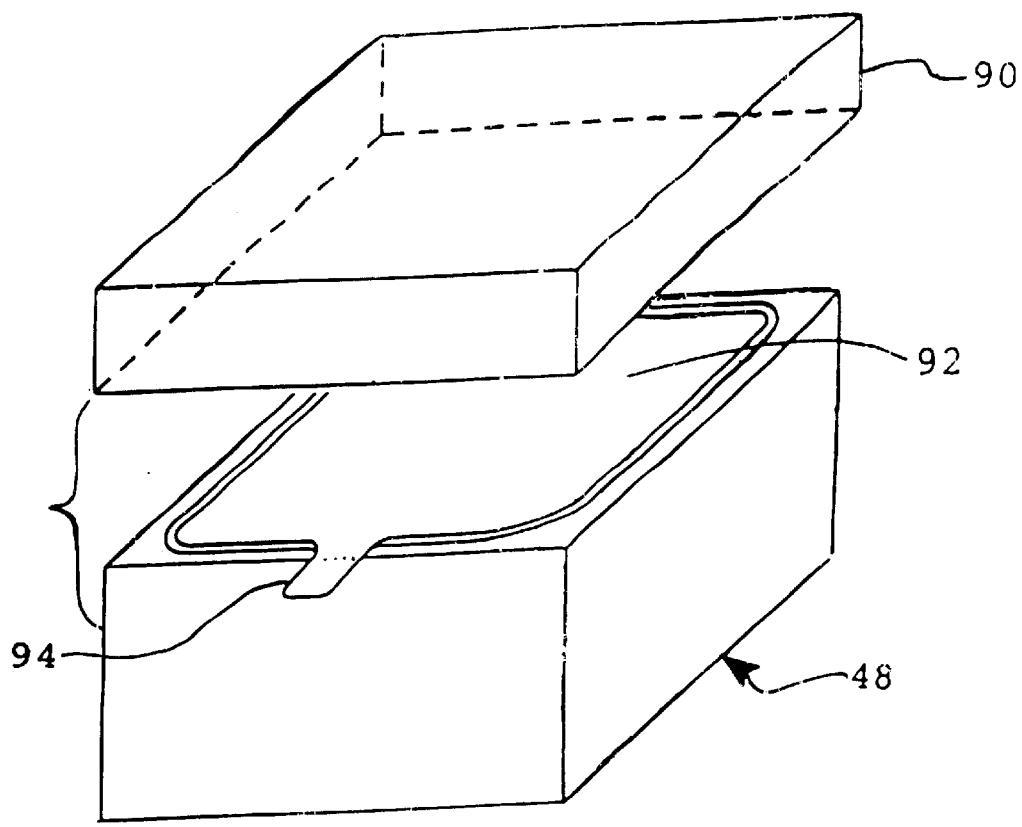
FIG. 18. This is a perspective view of the box which is to be filled with dissolvent and absorbent for mobile vehicle and household uses to dispose of thin medical sharps.
Figure 19:
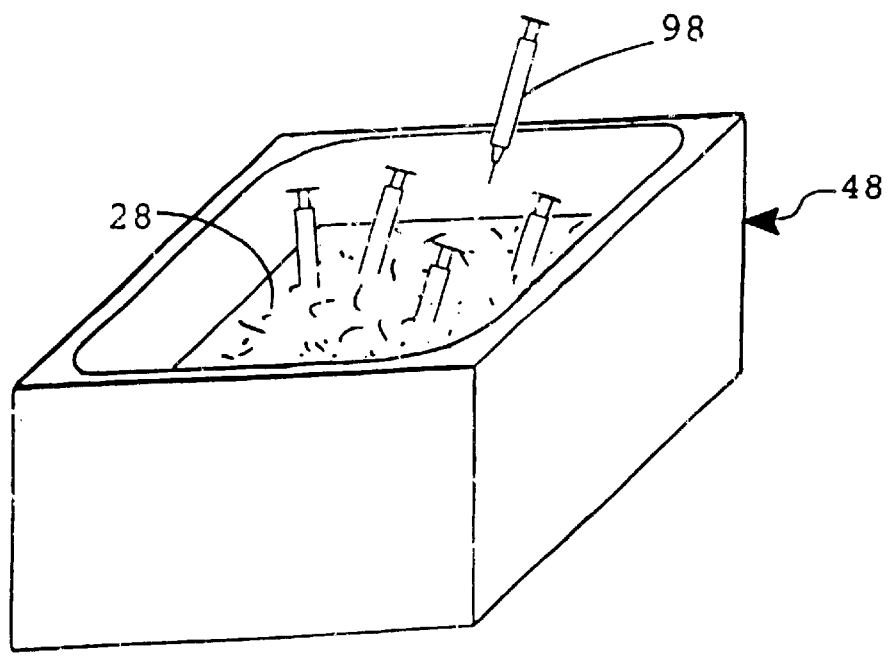
FIG. 19. This is a perspective view of the disposal container as in Figure 18 above with sealing lid removed to show used syringes being placed point downwards in the absorbent containing dissolvent.
Figure 20:
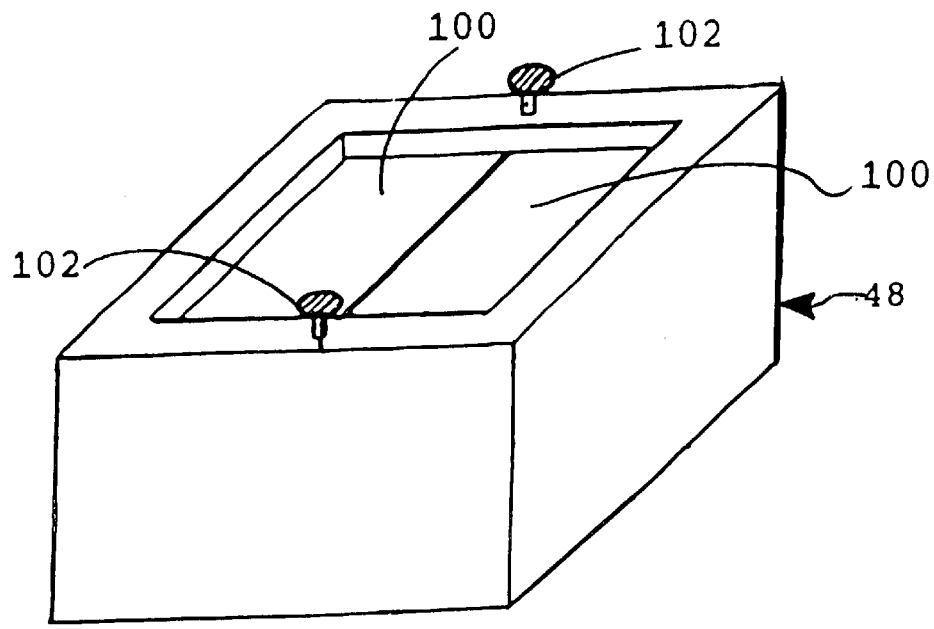
FIG. 20. This is a perspective view of a disposal container with a lid that can open when a button is pushed.
Figure 21:
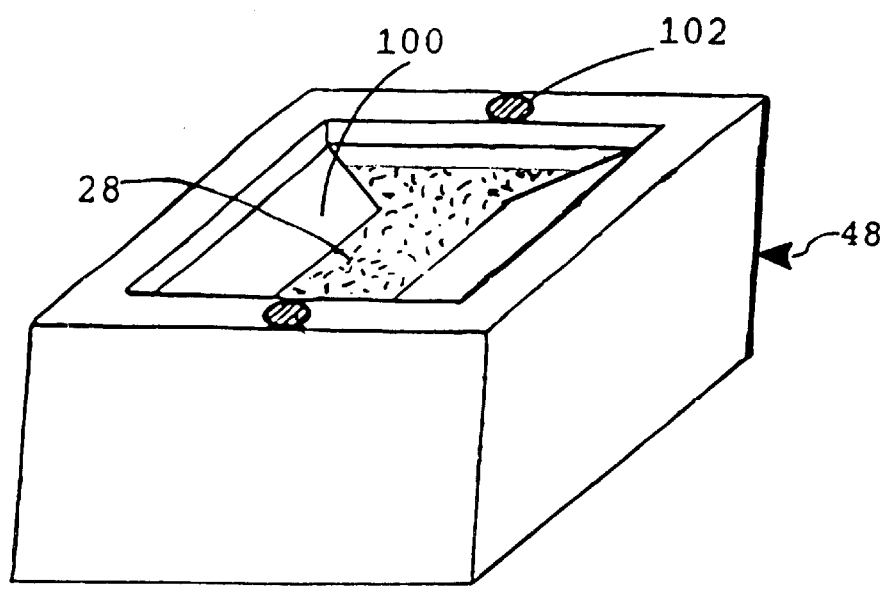
FIG. 21. This is a perspective view of the disposal container as in Figure 20 above with the lid open and the absorbent containing dissolvent exposed to view.
Figure 22:
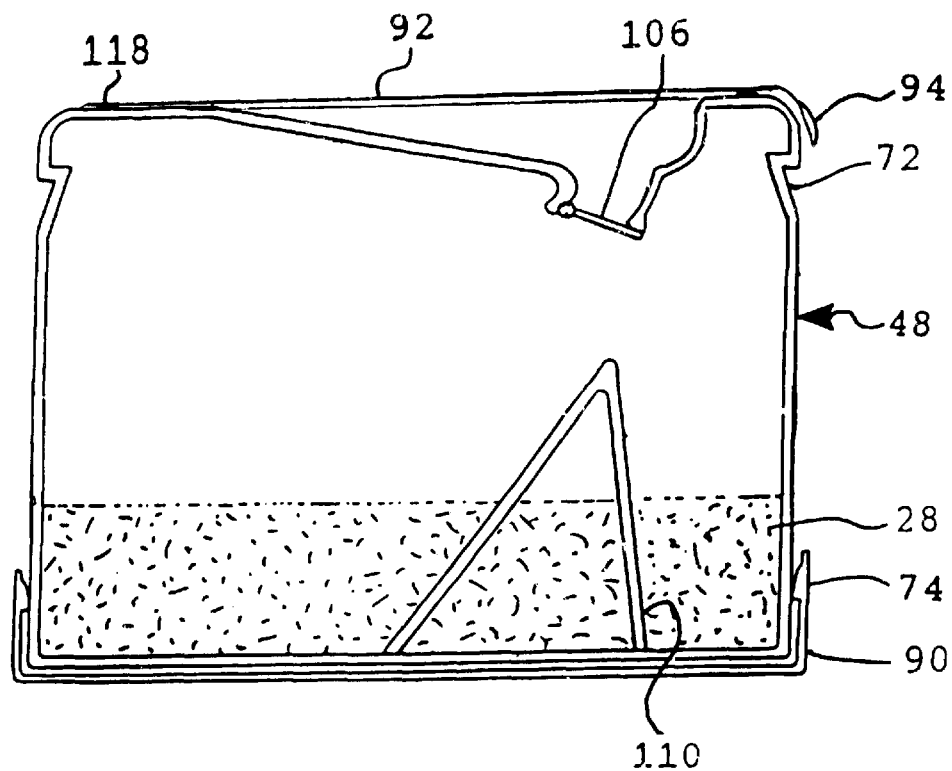
FIG. 22. This is a side view of a disposal container wherein used syringes will fall through the top section into the absorbent containing dissolvent. A locking cover lid for use when finished is shown located beneath the disposal container.
Figure 23:
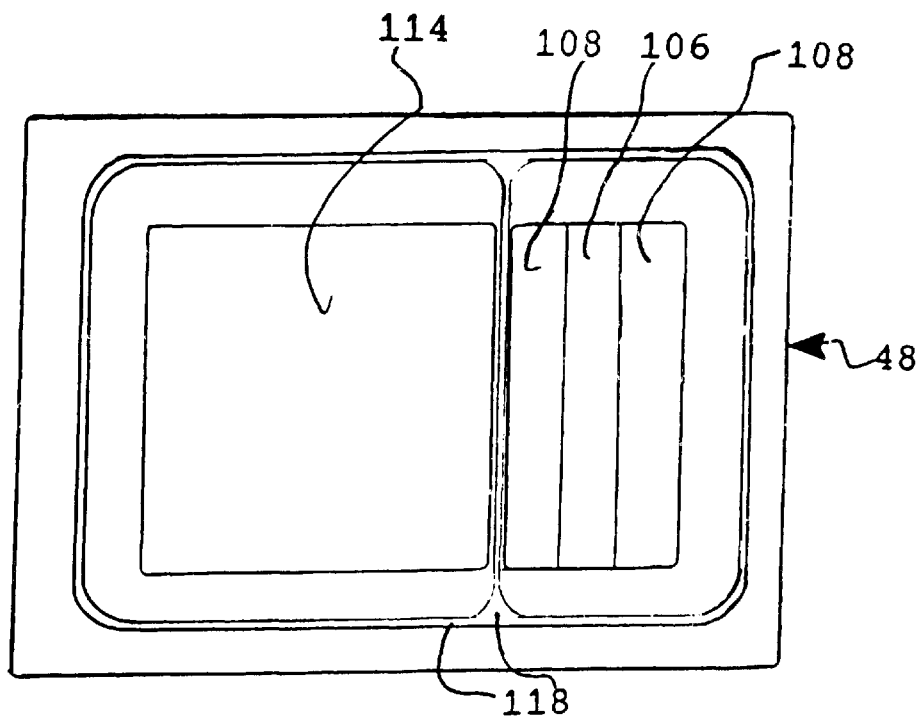
FIG. 23. This is a top view looking down upon the disposal container as in Figure 22 above wherein the used syringes will pass into the absorbent containing dissolvent.
Figure 24:
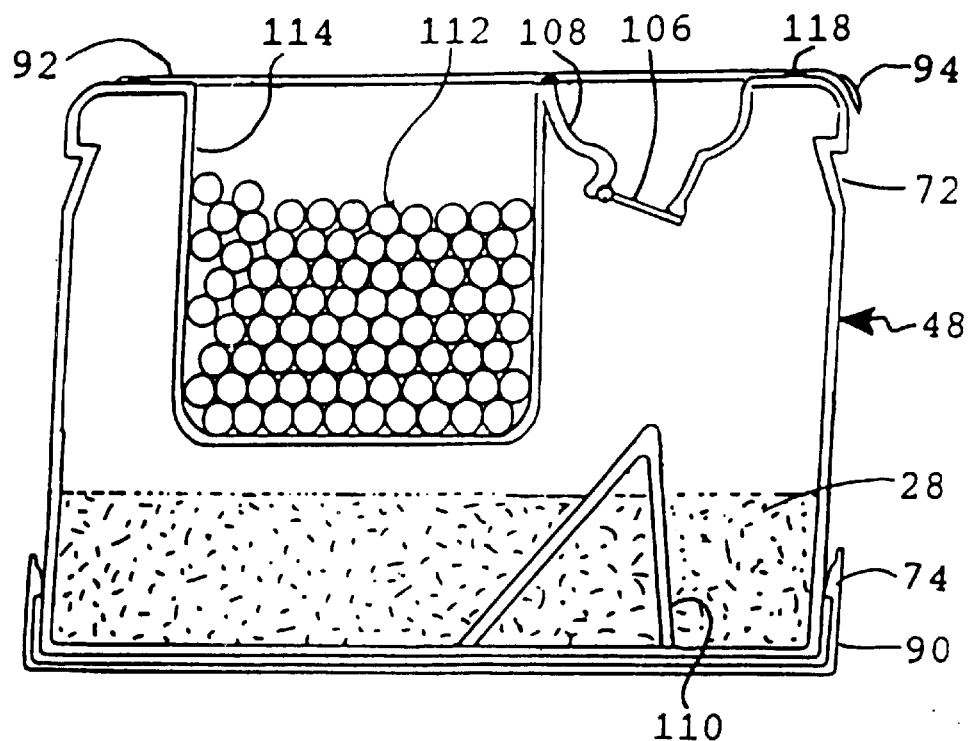
FIG. 24. This is a side view of a disposal container with sealing lid off showing a separate containment area for new syringes which when after use are inserted into the absorbent containing dissolvent.
Figure 25:
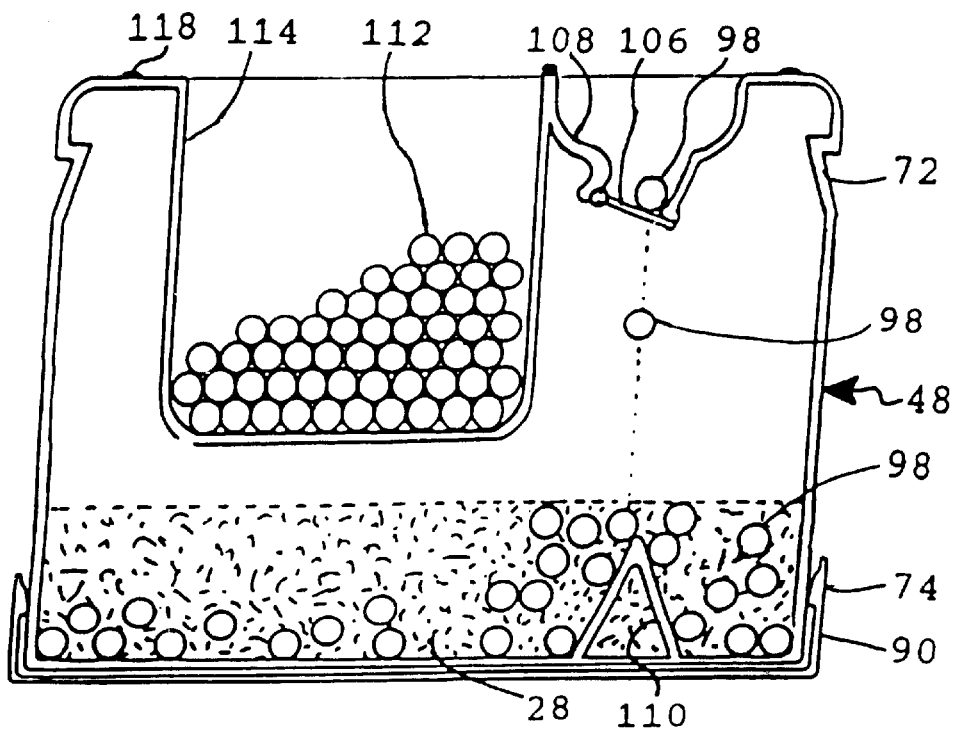
FIG. 25. This is a side view of a disposal container as in Figure 24 above showing examples of used syringes inserted into the absorbent containing dissolvent.

In FIG. 8 is shown a disposal container 48 for disposal of multiple used syringes and lancets and other small medical sharps. Section 50 is typically a cylindric plastic tub into which is fitted a conical bowl 52 providing a reservoir 54 for dissolvent 56 in the bottom. An absorbent 58 may be used in the reservoir to reduce the chance of spilling dissolvent if the container is upset. A conical guide 60 provides a concentric slot 62 into which syringes 64 or lancets 66 may be inserted. Radial supports 68 hold guide 60 in place over bowl 52. A cover 70 is provided which fits underneath section 50 when in use, and which fits on the top of section 50 after container 48 is full and ready for final disposal. A locking groove 72 in cover 70 serves to lock the cover in place.

In summary the higher the use and requirements for its use, the stronger the dissolvent can be formulated for this requirement. If 12 hours is a safe activity in low use situations, then the mildest dissolvents can be formulated. When speed and absolute activity are required as in emergency rooms and possibly operating rooms, a stronger dissolvent may be required. The formulations in each situation can be adjusted to meet each requirement in a proper and safe manner.

We claim:

1. A self-disposing medical hypodermic syringe comprising:
   a tubular barrel;
   a metal hypodermic needle attached to said barrel to receive fluid therefrom;
   a plunger fitted into and slideable within said barrel with the means to eject fluid through said needle; and
   an associated capsule containing a dissolvent and having means for application of said dissolvent to said needle after use of said hypodermic whereby said needle is chemically disposed of by said dissolvent.

2. The self-disposing medical hypodermic syringe as in claim 1 wherein said capsule further comprises a conventional safety cap defining a chamber for protection of the needle prior to use of the syringe.

3. The self-disposing medical hypodermic syringe as in claim 2 wherein said capsule further comprises means providing for the transfer of said dissolvent from said capsule into said chamber after the syringe has been used and recapped whereby the dissolvent surrounds and dissolves said hypodermic needle.

4. The self-disposing medical hypodermic syringe as in claim 2 wherein said syringe further comprises a lanyard attachment connecting the capsule to the syringe.

5. The self-disposing medical hypodermic syringe as in claim 1 wherein said dissolvent comprises a solution of at least one acid and at least one salt capable of chemically dissolving a thin metallic sharp such as a metal hypodermic needle.

6. The self-disposing medical hypodermic syringe as in claim 1 wherein said dissolvent comprises a solution containing at least one acid, a non-ferrous salt, and water.

7. The self-disposing medical hypodermic syringe as in claim 1 wherein said dissolvent comprises a solution of at least one acid, water, and a chloride selected from the group consisting of an aqueous metal chloride, iron trichloride, iron perchloride, and a chloridized metal compound.

8. The self-disposing medical hypodermic syringe as in claim 1 wherein said dissolvent comprises a solution of a chloride, water, and at least one acid selected from the group consisting of hydrochloric, sulfuric, nitric, hydrofluoric, phosphoric, oxalic, acetic, carbolic, and acids that in the solution can dissolve a metallic medical sharp.

9. The self-disposing medical hypodermic syringe as in claim 5 wherein said dissolvent further comprises an accelerant to accelerate the chemical dissolution of a metallic medical sharp.

10. The self-disposing medical hypodermic syringe as in claim 2 and further comprising an absorbent within said chamber and said absorbent is selected from the group of fibrous materials consisting of wool, cotton, silk, flax, hemp, jute, kapok, ramie, sisal, mohair, wood, paper, wood cellulose, plastic fiber, rayon, acetate, olefin, acrylic, polyester, and polyamide.

11. The self-disposing medical hypodermic syringe as in claim 10 wherein said absorbent further comprises abrasive particles having a hardness greater than the hardness of said hypodermic needle so the needle will be scratched by said abrasives as the needle is inserted into said chamber.

12. The self-disposing medical hypodermic syringe as in claim 2 and further comprising an absorbent within said chamber and said absorbent is selected from the group of materials consisting of sponges, mosses, peat moss, diatomaceous earth, artificial sponges, and animal litter.

13. The self-disposing medical hypodermic syringe as in claim 3 wherein said means providing for said transfer comprises a flexible bulb containing said dissolvent whereby squeezing said bulb transfers dissolvent into said chamber.

14. The self-disposing medical hypodermic syringe as in claim 3 wherein said means providing for said transfer comprises a cylinder containing dissolvent in one end of said cap and a plunger fitted into and slidable within said cylinder with the means to transfer dissolvent into said chamber when said plunger is depressed.

15. The self-disposing medical hypodermic syringe as in claim 2 wherein said cap further comprises and defines a second chamber for capping over said needle after use and means provide for said dissolvent to act on said needle within said second chamber.

16. The self-disposing medical hypodermic syringe as in claim 15 wherein said cap further comprises means providing permanent fitment over said needle once said capping is effected.

17. Device for disposing metal medical sharps, consisting of:
   a receptacle operable to receive said metal medical sharps; and
   a chemical dissolvent contained within said receptacle, said dissolvent having water, acid and a salt, wherein the dissolvent will chemically dissolve the metal medical sharps after use.

18. The device for disposing as in claim 17, wherein said receptacle further comprises caps or containers.

* * * * *